United States Patent
Matsuura et al.

(10) Patent No.: US 9,770,020 B2
(45) Date of Patent: Sep. 26, 2017

(54) INSECT PEST REPELLANT

(71) Applicant: MORISHITA JINTAN CO., LTD., Osaka-shi, Osaka (JP)

(72) Inventors: Kenji Matsuura, Kyoto (JP); Daisuke Tagawa, Hirakata (JP); Ryosei Kamaguchi, Hirakata (JP); Masaaki Nakatsuji, Hirakata (JP); Taku Hashimoto, Hirakata (JP)

(73) Assignee: MORISHITA JINTAN CO., LTD., Osaka (JP)

( * ) Notice: Subject to any disclaimer, the term of this patent is extended or adjusted under 35 U.S.C. 154(b) by 0 days.

(21) Appl. No.: 14/358,580

(22) PCT Filed: Nov. 16, 2012

(86) PCT No.: PCT/JP2012/079813
§ 371 (c)(1),
(2) Date: May 15, 2014

(87) PCT Pub. No.: WO2013/073676
PCT Pub. Date: May 23, 2013

(65) Prior Publication Data
US 2014/0328886 A1    Nov. 6, 2014

(30) Foreign Application Priority Data

Nov. 16, 2011   (JP) ................. 2011-250494

(51) Int. Cl.
*A01N 25/26* (2006.01)
*A01M 1/20* (2006.01)
*A01N 25/18* (2006.01)
*A01N 63/02* (2006.01)
*A01N 43/54* (2006.01)
*A01N 57/20* (2006.01)
*A01N 61/00* (2006.01)

(52) U.S. Cl.
CPC .......... *A01N 25/26* (2013.01); *A01M 1/2011* (2013.01); *A01N 25/18* (2013.01); *A01N 43/54* (2013.01); *A01N 57/20* (2013.01); *A01N 61/00* (2013.01); *A01N 63/02* (2013.01)

(58) Field of Classification Search
CPC ..... A01M 1/2011; A01N 61/00; A01N 25/26; A01N 63/02; A01N 25/18; A01N 57/20; A01N 43/54; A01N 25/28
See application file for complete search history.

(56) References Cited

U.S. PATENT DOCUMENTS

2010/0028323 A1   2/2010   Matsuura et al.
2011/0091409 A1   4/2011   Matsuura

FOREIGN PATENT DOCUMENTS

| JP | 2000-342149 | 12/2000 |
| JP | 4126379 | 5/2008 |
| JP | 2008-184391 | 8/2008 |
| JP | 2009-51748 | 3/2009 |
| WO | WO 2011/059054 | 5/2011 |

OTHER PUBLICATIONS

"Termites and strategies of extermination", published by The Japan Termite Control Association, 2000, pp. 218-220, and English translation.

Yoshimura et al. "Activity Evaluation of Underground Termites in Japan using Monitoring Station and Method for repelling Termites by Bait Method", New Development of Monitoring Technique of Insects Ecology in Living Space, 2006, p. 48-53, and English translation.

*Primary Examiner* — Robert Cabral
(74) *Attorney, Agent, or Firm* — Hamre, Schumann, Mueller & Larson, P.C.

(57) ABSTRACT

The present invention provides an insect pest repellant and a method for repelling insect pest using the same, which is highly transported by the insect pests and which effectively exterminates insect pests and does not badly affect ecological system. The present invention is to provide an insect pest repellant comprising, in a mixed condition, (A) a dummy egg imitating an egg of an insect pest, formed from a particulate substrate on which an egg recognizing pheromone is coated, and (B) a particle containing an active component for repelling the insect pest either on a surface or in an inside of the particle.

11 Claims, 3 Drawing Sheets

INSECT PEST REPELLANT

TECHNICAL FIELD

The present invention is related to an insect pest repellant for repelling an insect pest, in particular a termite, and a method for repelling the insect pest using the same.

BACKGROUND ART

A method for repelling insect pests has been studied so far. Especially, since termites damage to wooden houses so much, a termite repellant or a termite repelling method has been intensely studied or developed in the world. The method for repelling termites includes a method for killing termites wherein a solvent type insecticide of organic phosphorus agent, carbamate agent, pyrethroid agent and the like is injected into an approach point of termites; and a method for killing termites wherein methyl bromide or the like is smoked (see Non-patent Literature 1, for example).

Instead of chemical spraying method, an insecticide having slow releasing properties is contained in food for termites and fed to termites, which is called "bait method" (see Non-patent Literature 2, for example).

In the method for repelling termites in the prior art, much amount of chemical substances is externally applied to woods which have damaged by termites, but the method would damage to human health, for example sick house syndrome, or to environmental pollution. In addition, such external application is difficult to totally kill the termites and a portion of the colony of termite would reproduce a colony and damages to the portions which have not been applied by chemicals. In the above methods, most serious problem is that the above mentioned repelling method necessitates much amount of labor to effectively kill termites. In addition, most often applied method for repelling termites is a smoking of methyl bromide which is, however, questioned as a material causing depletion of ozone layer and is recently tried to inhibit the use methyl bromide.

Ants similar to termites which form social living are generally repelled by feeding favorite foods containing chemical substance toxic to ants and transporting the foods by the ants to their nest to kill all colonies of ants. However, since termites feed woods which termites are nested therein, it is very difficult to externally feed favorite food containing insecticide to termites and therefore the bait method as mentioned above is not effective to termites. Especially, it is very difficult to totally kill all nests of termites belonging to *Reticulitermes speratus* by the bait method (see Non-patent Literature 2).

As a method in which active component is effectively fed by insect pests in comparison with the bait method, an insect pest repellant method using dummy egg transportation has been developed using an egg-transporting instinct of one of basic social behavior of insect pests (see Patent Literature 1). The insect pests of Patent Literature 1 can be termites. However, the method of Patent Literature 1 employs crude extracted component extracted from eggs of termites, which makes it possible to transport dummy eggs by the termites, but this method does not employ egg recognizing pheromone of the termites. This method would not work so much in view of cost, unless egg recognizing pheromone of termites is identified and cheaply produced in large scale.

The present inventors already proposed in Patent Literature 2 dummy eggs for repelling termites comprising an egg recognizing pheromone and insect pests repellant of termites, because the egg recognizing pheromone of termites was identified as lysozyme, its salt, its biological fragment or peptide related to lysozyme. The dummy eggs were transported by termites to show excellent termite repellant effect. The present inventors are to enhance the properties of the dummy eggs to kill termites.

CITATION LIST

Patent Literature

[PTL 1]
JP-A 2000-342149
[PTL 2]
JP-A 2008-194007

Non Patent Literature

[NPL 1]
"Termites and Control Measures", published by Corporation Japan Termite Control Association, 2000, p. 219.
[NPL 2]
"Activity Evaluation of Underground Termites in Japan using Monitoring Station and Method for repelling Termites by Bait Method", New Development of Monitoring Technique of Insects Ecology in Living Space, 2006, p. 48.

SUMMARY OF INVENTION

Technical Problem

The present inventors have intensely studied the technique of Patent Literature 2 and have found that a transporting rate of dummy eggs by insect pests, especially termites, are varied by sorts of substrates of the dummy eggs. The present invention has been accomplished based on the new knowledge and is to provide an insect pest repellant, especially a termite repellant, which completely exterminates insect pests and does not badly affect ecological system.

Solution to Problem

The present invention is to provide an insect pest repellant comprising, in a mixed condition, (A) a dummy egg imitating an egg of an insect pest, formed from a particulate substrate on which an egg recognizing pheromone is coated, and (B) a particle containing an active component for repelling the insect pest either on a surface or in an inside of the particle.

In order to suitably conduct the present invention, it is preferred that the dummy egg (A) and the particle (B) are adhered or glued to each other.

Further, it is preferred that the active component for repelling the insect pest contained in the particle (B) is selected from one or more group consisting of an insecticide component, an incubation inhibitor, a reproduction inhibitor and a growth inhibitor.

It is also preferred that the substrate of the dummy egg (A) is formed from inorganic material.

It is further preferred that the particle (B) is a seamless capsule.

In the present invention, it is preferred that the insect pest is a termite.

It is also preferred that the insect pest repellant, which comprises (A) a dummy egg imitating an egg of an insect pest, formed from a particulate substrate on which an egg recognizing pheromone is coated and (B) a particle containing an active component for repelling the insect pest either on a surface or in an inside of the particle, in a mixed condition, is supplied to the insect pest and is carried by the insect pest to its nest by an egg transporting behavior.

Advantageous Effects of Invention

The present inventors have found that termites show high transporting rate of dummy eggs in the case where a substrate of the dummy eggs is inorganic material, especially glass, and that they do not transport dummy eggs so much in the case where the substrate is not inorganic material. In the present invention, inorganic material, especially glass, is used as substrates of dummy eggs. It is, however, difficult to have an active component for repelling insect pests in the dummy eggs using inorganic material as substrates, especially to enclose it in the dummy eggs. The active component for repelling insect pests is then put in a material which easily contains it, especially a capsule formed from gelatin, and the dummy eggs are mixed with the material containing the active component. The insect pests can carry or transport the material containing active component together with the dummy eggs into their nest in high probability, thus enhancing insect pests repelling effects.

In the present invention, if the dummy eggs (A) is adhered or glued to the particles (B) which contains the active component for repelling the insect pests, the insect pests (especially termites) carry and transport the dummy eggs (A) into their nest and naturally the particles (B) attached to the dummy eggs (A) would be also transported into the nest with the active component for repelling the insect nests. This embodiment can very effectively put the active component for repelling insect pests in their nest and the insect pests repellant of the present invention is very excellent in repelling effects.

DESCRIPTION OF EMBODIMENTS

The insect pests repellant of the present invention is characterized by comprising (A) a dummy egg imitating an egg of an insect pest, formed from a particulate substrate on which an egg recognizing pheromone is coated, and (B) a particle containing an active component for repelling the insect pest either on a surface or in an inside of the particle, in a mixed condition. The insect pests repellant of the present invention and the method for repelling insect pests using it are explained hereinafter in details.

The insect pests (such as termites) which have nature that they carry or transport their eggs in their nest to pile them up and lick surfaces of eggs to take care of them. They also lick with one other to exchange nutrition. The nature can be utilized to repel insect pests. For example, termites have nature that they carry and transport dummy eggs which have similar size and similar shape to their eggs and have egg identifying pheromone covering thereon, to a portion of piles of eggs in their nest, because they consider the dummy eggs as their eggs. In the nest, they look after their eggs including the dummy eggs and lick their surface. They also lick with each other to exchange nutrition. Accordingly, particles which contain an active component for repelling insect pests, such as incubation inhibitor, reproduction inhibitor, growth inhibitor and the like, are transported to their pile of eggs together with the dummy eggs, to effectively destroy a center of reproduction.

The insect pests repelled by the insect pests repellant of the present invention and by the method for repelling the insect pests using it include any insect pests which have nature of transporting their eggs based on egg recognizing pheromone. The insect pests, to which the insect pests repellant of the present invention and the method for repelling the insect pests of the present invention are effectively applied, are termites. Termites repelled by the present invention can be any type or any sort of termites which live not only in Japan but also in the world. Representative examples of the termites which preferably are repelled by the present invention are not limited thereto, but include, for example, *Reticulitermes speratus* termites, Formosan subterranean termites (*Coptotermes*) and the like. The term "to repel" used herein means both to destroy and to prevent or to eliminate. The term "insect pests" employed herein means insects which badly damage people, domestic animals, agricultural produces, property and the like.

(A) Dummy Eggs Imitating Eggs of Insect Pests, Formed from Particulate Substrate on which an Egg Recognizing Pheromone is Coated The egg recognizing pheromone used for the dummy eggs of the present invention includes, for example, lysozyme, a salt thereof, a biological fragment thereof and a relative peptide. The lysozyme can be derived from any living creatures, such as mammals, birds, fishes, reptiles, amphibians, insects (e.g. silkworms) and the like. The lysozyme can preferably be lysozyme derived from egg white of chickens, which can be cheap and be mass-produced. The lysozyme of the present invention can be one derived from an extract of termite eggs. The lysozyme of the present invention can either be purified or not purified. The lysozyme used for the present invention can also be one that is obtained by a gene recombinant method. The gene recombinant method which produces protein, polypeptide or peptide is known to the art. A gene of a desired protein is connected to a vector which is introduced into a host cell such as *Escherichia coli* or yeast, and the host is increased, to obtain the desired protein. Sorts of vector or host, conditions for introducing into a vector, conditions for increasing a host cell, separating or purifying method of the desired protein can be preferably selected by art-known materials or methods.

The lysozyme as mentioned above can be in the form of a salt. The lysozyme salt includes, for example a salt of any substance forming a salt with lysozyme, such as a salt of an organic acid, an inorganic acid, an organic base, an inorganic base and the like. The β- or γ-carboxylic group of aspartic acid or glutamic acid constituting lysozyme may be bonded with a metal, such as sodium or potassium to form a salt. The basic amino acid constituting lysozyme may form a salt in its side chain. The biological fragment of lysozyme or the lysozyme related peptide may be in the form a salt.

In addition, the biological fragment of lysozyme can be used as egg recognizing pheromone. The biological fragment of lysozyme means a polypeptide or peptide having a partial amino acid sequence of lysozyme having same egg recognizing activity with lysozyme. The biological fragment can be produced in large scale by gene recombinant method, due to the fragment being short chain.

Further, the lysozyme related peptide can also be used as the egg recognizing pheromone. The lysozyme related peptide is protein, polypeptide or peptide which has same egg recognizing activity with lysozyme and is different from the above mentioned biological fragment of lysozyme. The lysozyme related peptide can be derived or produced either from natural substance or artificially. The lysozyme related peptide can also be an amino acid sequence which is different from natural lysozyme and is obtained by portion specific gene mutation method. For example, lysozyme, a biological fragment of lysozyme or a lysozyme related peptide that has an amino acid sequence favorable with termites is produced and employed. In addition, lysozyme, a biological fragment of lysozyme or a lysozyme related peptide that has an amino acid sequence specific to a specific sort of termites is produced and employed.

Another egg recognizing pheromone used for the dummy egg (A), formed from particulate substrate on which an egg recognizing pheromone is coated, includes, for example, β-glucosidase, a biological fragment of the β-glucosidase or a related peptide of the β-glucosidase. The β-glucosidase is present in microorganisms, plants or animals and can be derived from any sorts, for example plants, such as almonds and sago; animals, such as termites, xylophagous cockroaches and snails; microorganisms, such as aspergillus, yeast, enterococcus, bacillus and the like, which are not limited thereto. The β-glucosidase can be either purified or not purified. The β-glucosidase can be obtained by a gene recombinant method. Production of protein, polypeptide or peptide of gene recombinant methods is well known to the art. Generally, a gene of a desired protein is connected to a vector which is introduced into a host cell such as *Escherichia coli* or yeast, and the host is increased, to obtain the desired protein. Sorts of vectors or hosts, conditions for introducing a vector, conditions for increasing a host cell, separating or purifying method of the desired protein can be preferably selected by art-known materials or methods.

The β-glucosidase as mentioned above can be in the form of a salt. The β-glucosidase salt includes, for example a salt of any substance forming a salt with β-glucosidase, such as a salt of an organic acid, an inorganic acid, an organic base, an inorganic base and the like. The β- or γ-carboxylic group of aspartic acid or glutamic acid constituting β-glucosidase may be bonded with a metal, such as sodium or potassium to form a salt. The basic amino acid constituting β-glucosidase may form a salt in its side chain. The biological fragment of β-glucosidase or the β-glucosidase related peptide may be in the form a salt.

In addition, the biological fragment of β-glucosidase can be used as egg recognizing pheromone. The biological fragment of β-glucosidase means a polypeptide or peptide having a partial amino acid sequence of β-glucosidase having same egg recognizing activity with β-glucosidase. The biological fragment can be produced in large scale by a gene recombinant method, due to the fragment being short chain.

Further, the β-glucosidase related peptide can also be used as the egg recognizing pheromone. The β-glucosidase related peptide is protein, polypeptide or peptide which has same egg recognizing activity with β-glucosidase and is different from the above mentioned biological fragment of β-glucosidase. The β-glucosidase related peptide can be derived or produced either from natural substance or artificially. The β-glucosidase related peptide can also be an amino acid sequence which is different from natural β-glucosidase and is obtained by portion specific gene mutation method. For example, β-glucosidase, a biological fragment of β-glucosidase or a β-glucosidase related peptide that has an amino acid sequence favorable with termites is produced and employed. In addition, β-glucosidase, a biological fragment of β-glucosidase or a β-glucosidase related peptide that has an amino acid sequence specific to a specific sort of termites is produced and employed.

The dummy egg (A) of the present invention, formed from particulate substrate on which an egg recognizing pheromone is coated, should have a shape, a size and a quality similar to an egg of an insect pest to be repelled. A shape and a size of the dummy egg (A) employed in the present invention should be imitated with an actual egg of the insect pest. In the case where the insect pest is a termite, the dummy egg (A) has a long egg shape or a spherical shape. It is preferred that, in the case of the long egg shape, the short diameter of it should be same with or a little larger than a short diameter of a termite egg. For example, an egg of a termite has a short diameter of about 0.25 to about 0.45 mm and a short diameter of the dummy egg can be within the range of about 0.25 to about 0.6 mm, preferably about 0.4 to about 0.55 mm. In the case of the egg having a spherical shape, the diameter of the dummy egg is same or larger than a short diameter of an egg of the termite. For example, an egg of a termite has a short diameter of about 0.25 to about 0.45 mm and a diameter of the dummy egg can be within the range of about 0.25 to about 0.6 mm, preferably about 0.4 to about 0.6 mm, more preferably about 0.45 to about 0.55 mm. The dummy egg (A) preferably has a spherical shape because it can be produced easily.

The dummy egg (A) of the present invention not only has physical properties, such as weight and hardness, in addition to shape and size as mentioned above, but also has chemical properties, especially the egg recognizing pheromone being same with a natural egg of an insect pest. Thus, when the dummy egg (A) is covered with an egg recognizing pheromone on its surface, it is necessary that the pheromone appears on the surface of the dummy egg.

The substrate of the dummy egg (A) of the present invention can be formed from any material which is similar to a natural egg of an insect pest in shape and properties, including inorganic material, such as glass, silicon dioxide, titanium oxide, titanium dioxide, aluminum (oxide), tin oxide, indium oxide, zinc oxide, antimony oxide, antimony-containing tin oxide, tin-containing indium oxide, iron (oxide) and the like.

According to the present invention, the egg recognizing pheromone is coated on the particulate substrate to form a dummy egg (A) imitating an egg of an insect pest. A coating method on the substrate can be anyone that is known to the art. The pheromone is dusted, coated, or sprayed on the substrate, or the substrate is dipped in the pheromone. When coating, the egg recognizing pheromone can be dissolved in water or a hydrophilic solvent, such as glycerin, alcohol and the like, or dispersed in a lipophilic solvent, such as N,N-dimethylformamide, dimethylsulfoxide, tetrahydrofuran, 1,4-dioxane and the like, which can operate coating easily and form a uniform coated film. In addition, since a method wherein protein, polypeptide or peptide is immobilized on a solid support is known to the art, the method can be applied as a coating method. The immobilizing method includes, for example, adsorption process, covalent bond method, ionic bond method, entrapping method, and the like.

An amount of the egg recognizing pheromone which is applied on the particulate substrate of the dummy egg (A) of the present invention can be determined by the art based on many factors, such as sorts of pheromone, physical or chemical properties, sorts of insect pests, sorts or amounts of insect repellant active components, sorts or degrees of desired technical effects.

In order to keep the activity of the egg recognizing pheromone as the dummy egg (A) of the present invention and keep the pheromone on the surface of the particulate substrate, the particulate substrate preferably contains glycerol and/or cellulase. Glycerol or cellulase is not always highly purified one. An amount of glycerol or cellulase in the substrate can be determined based on many factors, such as sorts, properties and mounts of pheromone, sorts of insect pests, sorts or amounts of active components for repelling insect pests, properties or degrees of technical effects. When glycerol or cellulase is applied on, for example, a surface of the particulate substrate, the dummy egg (A) is bonded or adhered to the particle (B) containing an active component for repelling the insect pests by mixing.

The substrate of the dummy egg (A) of the present invention preferably contains a component eluted from the eggs of insect pests to be repelled. This makes egg-transporting effects higher. A crude extract from eggs of insect pests can be contained in the substrate or its purified one can be contained in the substrate. An amount of the extract or purified extract can be determined based on many factors, such as sorts, properties or amount of the egg recognizing pheromone, sorts of insect pests, sorts or degrees of technical effects, and the like. Extracting method or purification method of effective components from eggs of insect pests is known to the art.

(B) Particle Containing an Active Component for Repelling the Insect Pest

The active component for repelling insect pest employed in the insect pest repellant and the method for repelling insect pest of the present invention can be anyone which repels the insect pests. For example, the active component for repelling the insect pests includes one which can disorder behavior of insect pests and can destroy its colony. The active component for repelling the insect pests includes insecticidal active component, incubation inhibitor, reproduction inhibitor, growth inhibitor, or the like. Sorts and amounts of the active component for repelling the insect pest, which is employed in the particle (B) contained in the insect pest repellant of the present invention, can be determined based on many factors, such as sorts of the active component, sorts of the insect pest, sorts and degree of the activity for repelling the insect pest (damage to be given to the insect pest) and the like. Generally, sorts and amounts of the active component for repelling the insect pest can be selected such that it sufficiently provides sufficient technical effects to the insect pest, but it should also be noted that they are selected such that it does not reduce a transporting rate of the dummy egg by the insect pest and it also does not adversely affect human beings who employ the insect pest repellant and the method for repelling the insect pest and does not adversely affect domestic animals and useful insects.

The active component for repelling the insect pests, employed in the particle (B) of the present invention, can be one sort or two or more sorts. Examples of the active components are insecticidal components, such as pyrethroid compound, organic phosphorus compound, carbamate compound, N-aryldiazole compound, hydrazone compound, sulphonamide compound, natural insecticidal component, and the like. The active component for repelling the insect pests may include insect growth regulator, such as chitin synthesis inhibitor, juvenile hormone analogous active compound, molting hormone analogous active compound and the like. The active components for repelling the insect pest, employed in the present invention are not limited to the above-mentioned components, although it goes without saying.

In the above particle (B) of the present invention, the active component for repelling the insect pest is preferred to be delayed acting. As mentioned above, the insect pest (e.g. termites) recognizes as its egg the dummy egg (A) which has similar size and shape to its natural egg and which has egg recognizing pheromone on its surface, and then transports the dummy egg (A) to an egg batch of its nest, wherein the particle (B) is adhered to the dummy egg (A). The insect pest generally conducts care behavior, such as licking a surface of the dummy egg (A) and simultaneously licking a surface of the particle (B), to take in the active component for repelling the insect pest. When some individuals of the insect pest in its colony take the active component on the particle (B) in, the active component would spread over a whole of the colony by frequent trophallaxis, such as stmodeal food to mouth feeding and proctodeal food. Accordingly, it is preferred that the active component for repelling the insect pest in the present invention does not show the repelling effects when the insect carries and transports the dummy egg (A) together with the particle (B) or immediate after the insect pest takes it in, or shows the repelling effects to such a degree that the transporting behavior or the trophallaxis is conducted by the insect pest, after which the repelling effects would be exhibited after the dummy egg (A) and the particle (B) are carried and transported to the nest of the insect and the trophallaxis is conducted between the individuals. By using the delayed acting active component for repelling the insect pest, many individuals in the colony of the target can be effectively repelled and a used amount of the active component can be reduced. Thus, it does not adversely affect another ecological system. The insect pest-repelling active component employable in the particle (B) of the present invention further includes, for example, delayed acting insecticidal component, such as hydramethylnon, trichlorfon and the like; delayed acting hatching inhibitor; delayed acting reproduction inhibitor; delayed acting growth inhibitor; and the like, but it is not limit thereto.

In the particle (B) of the present invention, a shell substrate of the particle (B) is preferably made by a controlled releasing material. By using the controlled releasing material, the insect pest-repelling active component is released slowly after the dummy egg (A) is conveyed into the nest and the insect pest takes it in. A seamless capsule can be exemplified as a preferred embodiment of the particle (B).

Figure 1:
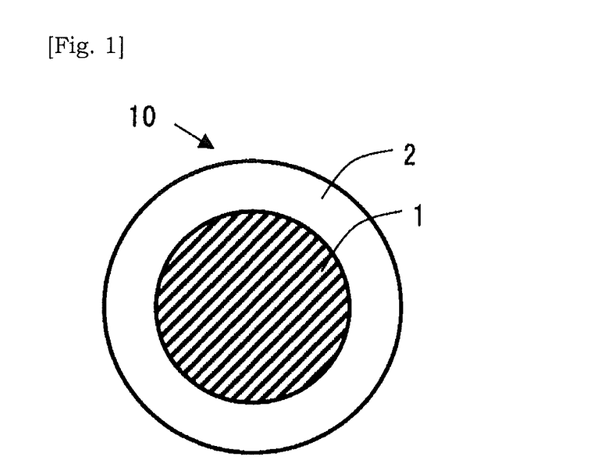
FIG. 1 schematically shows a cross sectional view of one embodiment of a particle (B) with two layers structure containing an active component for repelling insect pests of the present invention in the form a seamless capsule.
Figure 2:
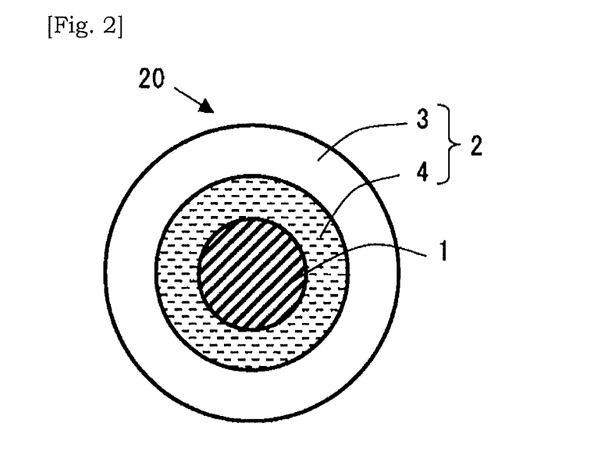
FIG. 2 schematically shows a cross sectional view of one embodiment of a particle (B) containing an active component for repelling insect pests of with three layers structure the present invention in the form of a seamless capsule.

The seamless capsule employable for the particle (B) containing the insect pest repelling active component is explained in details by using FIGS. 1 and 2. FIG. 1 is a general cross sectional view which schematically shows one embodiment (two layers construction) of the particle (B) being a seamless capsule which contains the insect pest repelling active component. FIG. 2 is a general cross sectional view which schematically shows another embodiment (three layers construction) of the particle (B) being a seamless capsule. The seamless capsule comprises an enclosed component (1) of the insect pest repelling active component and a shell material layer (2) enclosing the enclosed material (1). A simplest construction of the above mentioned seamless capsule is one having the two layers structure in which one layer of a shell material layer (2) is employed, as shown in FIG. 1.

The shell material layer (2) is formed from a shell substrate of a natural polymers, such as gelatin, agar, carrageenan, cellulose or a derivative of cellulose, chitin, chitosan, hydrolyzed starch, shellac, alginic acid; synthetic polymers, such as acrylate type oligomer, methacrylate type oligomer, unsaturated polyester type oligomer, vinyl ether type oligomer, unsaturated polyamide oligomer; and the like, which is used solely or in combination.

The shell substrate of the shell material layer (2) may preferably be gelled by temperature change or irradiation of ultraviolet light when preparing the seamless capsule. The substrate which cures by temperature change includes thermoplastic substrate or thermocurable substrate.

The shell material of the seamless capsule may contains a plasticizer and a colorant in addition to the above mentioned substrate. The plasticizer includes water soluble polyhydric alcohol or a water soluble derivative thereof. An amount of the plasticizer may be within the range of 1 to 50% by mass, more preferably 3 to 30% by mass, based on a total weight of the shell material layer. Amounts of less than 1% by mass do not provide sufficient plasticizing effects and those of more than 50% by mass easily soften and adhere with each other capsule.

Examples of the water soluble polyhydric alcohol and water soluble derivative thereof include glycerin, polyglycerin, sorbitol, ethylene glycol, polyethylene glycol, propylene glycol, polypropylene glycol, ethylene oxide-propylene oxide copolymer, oligosaccharide, sugar ester, sorbitan ester and the like, which is not limited thereto.

The shell substrate of the shell material of the seamless capsule may preferably be contained in an amount of 1 to 50% by mass, more preferably 10 to 30% by mass, based on a total weight of the shell material. If it is contained in an amount of less than 1% by mass, the resulting shell does not have sufficient strength of gel. If it is more than 50% by mass, a solution of the shell material has too high viscosity and does not form capsules.

The seamless capsule having the two layers structure can be produced by pouring an enclosed component composition through an inner nozzle and pouring a shell material composition through an outer nozzle simultaneously into a carrier flowing liquid. According to the particle (B) of the present invention, in order to let the active component to be controlled releasing, the shell material layer (2) is made two layers of a shell inner layer (4) as a protective layer and a shell layer (3), to form a seamless capsule having the three layers structure.

Figure 3:
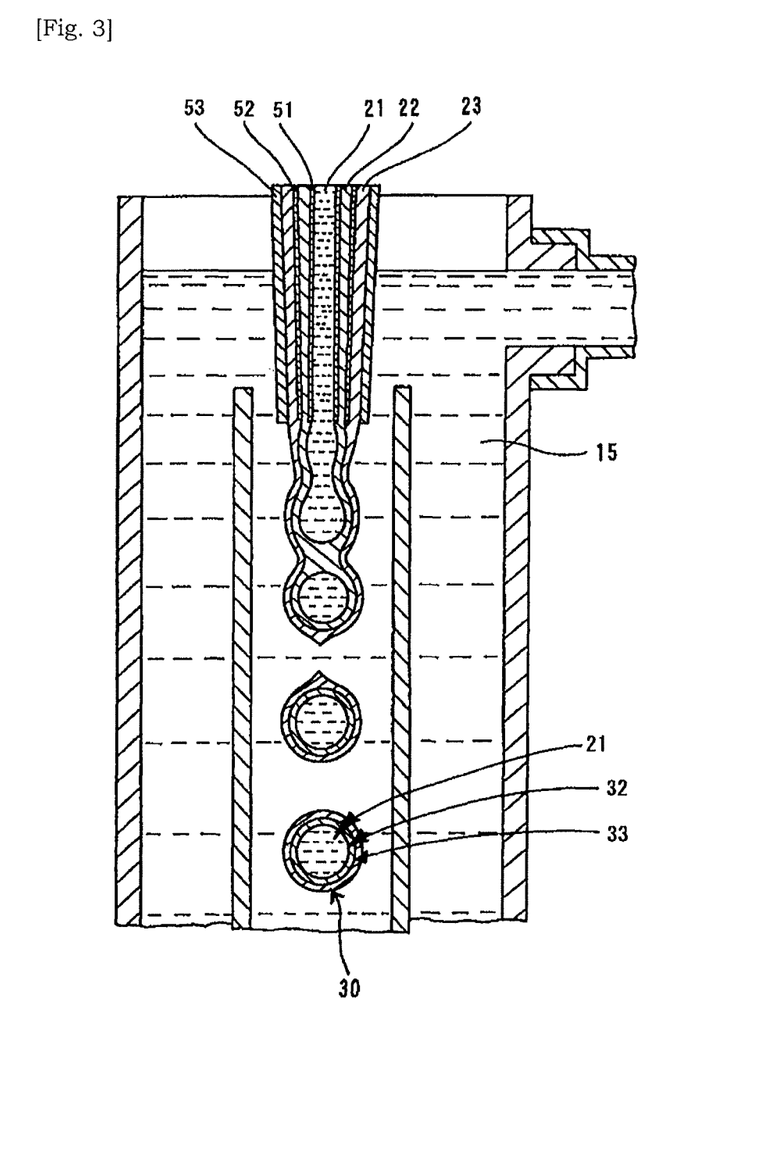
FIG. 3 schematically shows a cross sectional view of a nozzle portion of an apparatus for producing seamless capsules with three layer structure containing an active component repelling insect pests of the present invention.

The seamless capsule having the three layers structure can be produced, as shown in FIG. 3, by providing an enclosed component composition (21) to an inner nozzle (51), providing a shell inner layer material (22) to an intermediate nozzle (52), providing a shell material composition (23) to an outer nozzle (53), and then pouring them from the ends of the nozzles simultaneously into a flowing-down carrier liquid (15), to form seamless capsules having the three layers structure (30) continuously. The carrier liquid includes, for example, medium-chain fatty acid triglyceride (MCT), plant oil (such as palm oil, sunflower oil, rapeseed oil, safflower oil, sesame oil, grape seed oil and a mixture thereof), silicone oil (such as dimethylsilicone), liquid paraffin and a mixture thereof. Details of the above steps and other materials to be used are described in JP 2007-145756 A.

In the seamless capsule having three layers structure consisting of the enclosed material, the protective layer for the enclosed material and the shell layer, a layer of an objective active component may be inserted between the protective layer and the shell layer, to form a seamless capsule having four layers structure. Each layer may also be made two or more layers to form a seamless capsule having more than four layers structure. A seamless capsule having four or more layers structure and its production are also described in JP 2007-145756 A.

In addition, the insect pest repelling active component which is lipophilic (hydrophobic) may be dispersed or solved in a solvent, such as medium-chain fatty acid triglyceride (MCT), plant oil (such as palm oil, sunflower oil, safflower oil, sesame oil, rapeseed oil, grape seed oil and a mixture thereof), silicone oil (such as dimethyl silicone), liquid paraffin, SAIB (sucrose acetate isobutyrate) and a mixture thereof. The insect pest repelling active component which is hydrophilic may be dispersed or solved in a solvent, such as polyethylene glycols, glycerin, propylene glycol, polypropylene glycol and a mixture thereof.

A shape, size and properties of the particle (B) containing the insect pest repelling active component of the present invention should be similar to those of an egg of the insect pest to be repelled. As mentioned above, the shape and size of the dummy egg of the insect pest imitate an egg of the insect pest to be repelled. In the case where the insect pest is termites, the dummy egg (A) has a shape of a long egg or a spherical shape. In order to carry the particle (B) together with the dummy egg, it is preferred that the particle (B) has substantially same shape, same size and same properties with the dummy egg (A). Accordingly, in the case of termites, it is preferred that the particle (B) should also be a long egg shape or a spherical shape.

As mentioned above, a size of the particle (B) is preferred to be similar to the dummy egg (A), but it is further preferred that the particle (B) is unremarkable to the insect pests and is same with or a little smaller than the dummy egg (A) in order to transport the particle (B) together with the dummy egg (A). For example, the size of the particle (B) is preferably within the range of about 0.25 to about 0.6 mm in short diameter, more preferably within the range of about 0.4 to about 0.55 mm in short diameter, in the case where the shape is a long egg shape. In the case where the particle (B) is sphere, the size of the particle (B) may be within the range of about 0.4 to about 0.6 mm, preferably about 0.4 to about 0.6 mm, more preferably about 0.45 to about 0.55 mm. It is preferred that the particle (B) is spherical same with the dummy egg, because it is easily produced.

Figure 4:
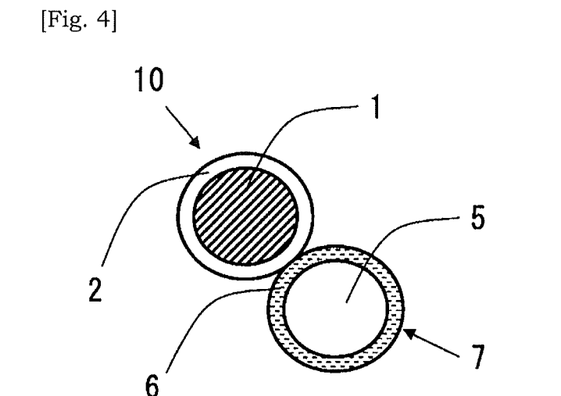
FIG. 4 schematically shows a cross sectional view of one embodiment of an insect pests repellant of the present invention.

The insect pest repellant of the present invention can be obtained by mixing the dummy eggs (A), formed from particulate substrates on which an egg recognizing pheromone is coated, with the particles (B) containing the insect pest repelling active component in the particles or on surfaces of the particles. One embodiment of the insect pest repellant of the present invention is characterized, as shown in FIG. 4, by comprising (A) a dummy egg (7) imitating an egg of the insect pest, formed from a particulate substrate (5) on which an egg recognizing pheromone (6) is coated, and (B) a particle (10) containing an insect pest repelling component (1) in the particle, having an embodiment of a seamless capsule consisting of an enclosed material (1) being an insect pest repelling active component (1) and a shell material layer (2) enclosing the active component (1), in the form of mixture.

A mixing ratio of the dummy egg (A) and the particle (B) containing the insect pest repelling active component may preferably be within the range of 1/1000 to 99/100, more preferably 1/100 to 50/100, most preferably 1/100 to 20/100 in A/B. The mixing ratios A/B of larger than 99/100 significantly reduce transporting effects of the insect pest repelling active component and those of less than 1/1000 reduce inducement effects of the dummy eggs to the insect pests and also transporting effects of the particles (B).

Generally, an insect pest (e.g. a termite) carries and transports one or more eggs one time and mixing of the dummy eggs (A) and the particles (B) is conducted uniformly so that the insect pests carry and transport them effectively. Mixing method of the dummy eggs (A) and the particles (B) can be anyone known to the art, as long as they are mixed uniformly.

In the insect pest repellant of the present invention, it is preferred that the dummy egg (A) is adhered or glued to the particle (B) containing the insect pest repelling active component and the insect pests carry and transport the dummy eggs (A) into its nest while the particles (B) containing the insect pest repelling active component are also transported into the nest, thus enhancing insect pest repelling effects by the active component. The adhering or gluing of the dummy eggs (A) and the particles (B) may be conducted by using an adhesive agent, such as gelatin, polyvinyl alcohol, casein, methylcellulose, carboxymethylcellulose, polyvinyl alcohol, polyvinyl pyrrolidone, sodium polyacrylate, potassium polyacrylate, silicone and the like. Adhesion strength is not necessary so strong, but is necessary to freely pick up such a number of particles from a mixture of the dummy eggs and the particles that the insect pests can carry and transport. As mentioned above, glycerol and the like may be applied to the dummy egg substrate in order to keep the activity of the egg recognizing pheromone in the dummy egg (A) of the present invention and to maintain the pheromone on the surface of the substrate, the substrate preferably contains glycerol and the like, but the glycerol can be used as an adhesive agent between the dummy eggs (A) and the particles (B). The above mentioned adhesive agent may be added to the glycerol to adhere the particles (B) to the dummy eggs (A).

In another embodiment of the present invention, the present invention provides a method for repelling an insect pest, wherein the insect pest repellant comprising, in a mixed condition, (A) a dummy egg imitating an egg of an insect pest, formed from a particulate substrate on which an egg recognizing material is coated, and (B) a particle containing an active component for repelling the insect pest either on a surface or in an inside of the particle is supplied to the insect pest. The insect pest to be repelled by the method of the present invention may be any insect pest as long as it has instinct of egg transporting behavior. The insect pests to which the method of the present invention is applied are termites. In the case where termites are repelled, the insect pest repellant comprising the dummy eggs (A), which imitate eggs of the insect pests and are composed of particulate substrates and egg recognizing pheromone covering the surface of the particulate substrates, and the particles (B) containing the insect pest repelling active component, in a mixed condition, is supplied to a termite passage or a portion of the nest. The insect pest repellant of the present invention is poured into the termite passage by making a hole in the termite passage. The insect pest repellant of the present invention may be covered with a protective film, such as cellophane and the like, to keep outside durability. In this case, the protective film may contain eating promoting material, such as wood extract, seasoned wood extract and the like. The method for repelling insect pests of the present invention may employ a monitoring station.

EXAMPLES

Preparation of Egg Recognizing Pheromone

Egg recognizing activity about a termite egg extract, a lysozyme purified from the termite egg extract, a proteinase-decomposed termite egg extract, an egg white lysozyme, cellulase, a mixture of the egg white lysozyme and cellulase, and a 30% aqueous solution of glycerin (a contrast), were determined by using *Reticulitermes speratus* workers (worker termites).

Each specimen was obtained as explained below.

An Eppendorf tube containing 400 mg of eggs of *Reticulitermes speratus* termites was charged with 800 μL of ultrapure water and homogenized, followed by applying ultrasonic waves thereto for 5 minutes. It was then subjected to a centrifugation separation at 15,000 rpm for 30 minutes and a supernatant liquid was freeze-dried to obtain freeze-dried powder. Next, 5.0 mg of the freeze-dried powder was dissolved in 100 μL of a 30% glycerin aqueous solution to obtain a termite egg extract.

The termite egg extract was purified by BioRex 70 cationic exchange resin (available from BioRad Laboratories, CA, U.S.A.) and then subjected to chromatography of Q-1 column (available from BioRad Laboratories, CA, U.S.A.) and Methyl HIC column (available from BioRad Laboratories, CA, U.S.A.) to separate lysozyme fragment. The lysozyme fragment was freeze-dried to obtain powder and 1.0 mg of the freeze-dried powder was dissolved in 20 μL of 30% glycerin aqueous solution (lysozyme separated from termite egg extract).

Proteinase K (available from Nacalai Tesque, Inc., Kyoto) was added to the termite egg extract and kept at 37° C. for 24 hours (proteinase-decomposed termite egg extract).

An egg white lysozyme (available from SIGMA, St. Louis, Mo., U.S.A.) of 2.0 mg was dissolved in 10 μL of a 30% glycerin aqueous solution to obtain an egg white lysozyme.

A cellulase (available from SIGMA, St. Louis, Mo., U.S.A.) of 2.0 mg was dissolved in 10 μL of a 30% glycerin aqueous solution to obtain a cellulase solution.

An egg white lysozyme of 10 mg and a cellulase of 10 mg were dissolved in 50 μL of a 30% glycerin aqueous solution to obtain a mixture of egg white lysozyme and cellulase.

Preparation of Seamless Capsule

Method 1: In the Case of Thermoplastic Resin Shell

A capsule producing apparatus having a concentric triple nozzle as shown in FIG. 3 was prepared and medium chain fatty acid triglyceride cooled to 8° C. was circulated in the apparatus as a carrier liquid 15. A shell composition 23 was poured from the outer nozzle 53 of the apparatus, a hydrophobic material 22 was poured from the intermediate nozzle 52, and an enclosed material-containing composition 21 was poured from the inner nozzle 21, simultaneously, into the carrier liquid 15, to form seamless capsules having the three layers structure (FIG. 2). It should be noted that, in the case where the enclosed material-containing composition 21 is hydrophobic, the apparatus can contain a concentric double nozzle and seamless capsules having two layers structure (FIG. 1) are obtained from only the enclosed material-containing composition and the shell composition.

The formed capsules were dried at a temperature of 25° C. and a humidity of 50% RH by an air ventilating rolling type dryer and subjected to the following evaluations.

Method 2: In the Case of Ultraviolet Curing Shell

A capsule producing apparatus having a concentric triple nozzle as shown in FIG. 3 was prepared and dimethyl silicone cooled to 15° C. was circulated in the apparatus as a carrier liquid 15. A shell composition 23 was poured from the outer nozzle 53 of the apparatus, a hydrophobic material 22 was poured from the intermediate nozzle 52, and an enclosed material containing composition 21 was poured from the inner nozzle 21, simultaneously, into the carrier liquid 15, to form liquid drops having the three layers structure. It should be noted that, in the case where the enclosed material-containing composition 21 is hydrophobic, the apparatus can contain a concentric double nozzle and seamless capsules having two layers structure (FIG. 1) are obtained from only the enclosed material-containing composition and the shell composition.

The formed liquid drops were irradiated by a metal halide lamp (wave length of 320 to 400 nm) to polymerize a light curable resin, thus forming seamless capsules. The resulting capsules were dried at a temperature of 25° C. and a humidity of 50% RH by an air ventilating rolling type dryer and subjected to the following evaluations.

Example 1

A shell composition was prepared from gelatin and polyethylene glycol (PEG #400 available from NOF Corporation, Japan) to form an aqueous solution of 60° C. containing 16% by weight of gelatin and 4% by weight of polyethylene glycol as solid content. An enclosed material-containing composition was a dimethyl silicone oil suspension of hydramethylnon. Seamless capsules having two layers structure were produced as mentioned in producing method of two layers structure capsules of Method 1. The resulting capsules had a diameter of 0.5 mm, a shell content of 40% by weight and a hydromethylnon final content of 0.5% by weight/particle. An amount equal to 50 glass beads having 0.5 mm was mixed with an amount equal to 50 seamless capsules obtained above to form a mixture, to which the egg recognizing pheromone was added and mixed well to coat the pheromone on the particles, thus forming an insect pest repellant.

Then, 20 particles of the insect pest repellant obtained above and 10 real termite eggs were randomly put on a dish having a diameter of 30 mm, to which 10 *Reticulitermes speratus* workers (worker termites) were also put in and kept at 25° C. for 24 hours in a temperature-controlled chamber, to determine a transporting rate of the insect pest repellant into egg batch. The worker termites picked up the eggs to form an egg batch in the dish to show protection behavior. A death rate of the termite in the dish was determined. The results are shown in Table 1.

Example 2

Seamless capsules were prepared as generally described in Example 1, with the exception that an aqueous solution of 70° C. containing a shell composition which composed 2.5% by weight of agar and 10% by weight of sorbitol in solid content was employed. They were evaluated by transporting rate of the insect pest repellant and death rate as described in Example 1. The results of the evaluation are shown in Table 1.

Example 3

A shell composition was prepared from an aqueous solution of 20% by weight of hydroxyethyl methacrylate monomer, 5% by weight of polyethylene glycol (PEG #600 available from NOF Corporation, Japan) and 0.5% by weight of a polymerization initiator 1-hydroxycyclohexyl phenyl ketone. An enclosed material-containing composition was prepared from a mixture of trichlorfon with polyethylene glycol (PEG #400 available from NOF Corporation, Japan). A protective layer was a hydrophobic material SAIB (sucrose isobutyrate acetate). Seamless capsules having three layers structure were prepared as generally described in Method 2. The resulting capsules had a diameter of 0.5 mm and a trichlorfon final content of 0.5% by weight/particle. An insect pest repellant was prepared as generally described in Example 1 and evaluations of transporting rate of the insect pest repellant and death rate were conducted as described in Example 1. The results of the evaluation are shown in Table 1.

Example 4

Seamless capsules were prepared as generally described in Example 3, with the exception that an aqueous solution containing a shell composition which was composed of 20% by weight of urethane acrylate (A-1000 available from Shin-Nakamura Chemical Co., Ltd.), 5% by weight of polyethylene glycol (PEG #400 available from NOF Corporation, Japan), and 0.5% by weight of a polymerization initiator 1-hydroxycyclohexyl phenyl ketone was employed. They were evaluated by transporting rate of the insect pest repellant and death rate as described in Example 1. The results of the evaluation are shown in Table 1.

Comparative Example 1

An amount equal to 100 glass beads having a diameter of 0.5 mm was mixed with 2.0 µL of the egg recognizing pheromone obtained above sufficiently to obtain dummy eggs formed from glass beads on which the egg recognizing pheromone was coated. Transporting rate of the dummy egg into egg batch and death rate of termites were evaluated as generally described in Example 1. The results of the evaluation are shown in Table 1.

Comparative Example 2

An amount equal to 100 glass beads having a diameter of 0.5 mm was mixed with 50 µg of hydramethylnon and 2.0 µL of the egg recognizing pheromone obtained above sufficiently to obtain dummy eggs comprising glass beads on which the insect pest repelling active component and the egg recognizing pheromone were coated. Transporting rate of the dummy egg into egg batch and death rate of termites were evaluated as generally described in Example 1. The results of the evaluation are shown in Table 1.

Comparative Example 3

Transporting rate of the dummy egg into egg batch and death rate of termites were evaluated as generally described in Comparative Example 2, with the exception that hydramethylnon was change to trichlorfon. The results of the evaluation are shown in Table 1.

Results of Evaluations

TABLE 1

| | Transporting rate (%) | Death rate of termites (%) |
|---|---|---|
| Example 1 | 100 | 100 |
| Example 2 | 100 | 100 |
| Example 3 | 100 | 100 |
| Example 4 | 100 | 100 |
| Comparative Example 1 | 100 | 0 |
| Comparative Example 2 | 48 | 48 |
| Comparative Example 3 | 38 | 51 |

In Examples 1 to 4, the insect pest repellant of the present invention, which comprises dummy eggs imitating eggs of insect pests having egg recognizing pheromone on a surface and particles containing insect pest-repelling active component in their inside, shows excellent results in which transporting rate of dummy eggs into egg batch by *Reticulitermes speratus* worker termites and death rage of worker termites in the dish are both 100%.

Comparative Example 1 only employs dummy eggs obtained by coating egg recognizing pheromone on glass beads. Accordingly, the transporting rate of the dummy eggs into egg batch is 100%, but the death rate of termites is 0%, because the dummy eggs do not contain any insect repelling active component. Comparative Examples 2 and 3 employ dummy eggs obtained by coating both egg recognizing pheromone and insect pest repelling active component on the glass beads. Accordingly, the transporting rate of them into the egg batch by termites is less than 50% and the death rate of termites is also very low.

INDUSTRIAL APPLICABILITY

The present invention provides effective insect pest repellant, especially termite repellant and is very useful in insect pesticide, insect pest repelling field, house construction and gardening field. The insect pest repellant of the present invention is also useful in biological studies.

REFERENCE SIGNS LIST

1: Enclosed material (insect pest repelling active component)
2: Shell material layer
3: Shell layer
4: Shell inner layer
5: Particulate substrate
6: Egg recognizing pheromone
7: Dummy egg
10: Particle (B) containing insect pest repelling active component, capsule having two layers structure
20, 30: Capsule having three layers structure, or liquid drop
15: Carrier liquid
21: Enclosed material-containing composition
22: Shell inner layer solution
23: Shell material solution
51: Inner nozzle
52: Intermediate nozzle
53: Outer nozzle.

The invention claimed is:

1. An insect pest repellant comprising, in a mixed condition, (A) a dummy egg imitating an egg of an insect pest, comprising a substrate, a surface of the substrate being coated with an egg recognizing pheromone, and (B) a particle comprising a shell and an active component for repelling the insect pest,
    wherein the active component is substantially contained inside the shell of the particle (B),
    wherein the dummy egg does not comprise the active component, and
    wherein the insect pest is a termite.

2. The insect pest repellant according to claim 1, wherein the dummy egg (A) and the particle (B) are joined to each other.

3. The insect pest repellant according to claim 1, wherein the active component for repelling the insect pest contained in the particle (B) is selected from one or more groups consisting of an insecticide component, an incubation inhibitor, a reproduction inhibitor and a growth inhibitor.

4. The insect pest repellant according to claim 1, wherein the particulate substrate of the dummy egg (A) is formed from inorganic material.

5. The insect pest repellant according to claim 1, wherein the particle (B) is a seamless capsule.

6. The insect pest repellant according to claim 1, wherein the insect pest is a termite.

7. A method for repelling an insect pest, wherein the insect pest repellant of claim 1 is supplied to the insect pest and is transported by the insect pest to its nest by an egg transporting behavior of the insect pest.

8. The insect pest repellant according to claim 5, wherein the seamless capsule comprises a shell component that permits controlled release of the active component from the particle (B).

9. The insect pest repellant according to claim 1, wherein the dummy egg has a shape selected from an elongate egg shape with a short diameter in the range of about 0.25 mm to about 0.6 mm, and a spherical shape with a diameter in the range of about 0.25 mm to about 0.6 mm.

10. The insect pest repellant according to claim 1, wherein the egg recognizing pheromone is present on the surface of the particle (B).

11. The insect pest repellant according to claim 1, wherein the shell of the particle (B) comprises a controlled releasing material for releasing the active component contained within the shell.

* * * * *